United States Patent [19]
Bershad

[11] Patent Number: 6,017,938
[45] Date of Patent: Jan. 25, 2000

[54] SHORT CONTACT TREATMENT FOR ACNE

[76] Inventor: Susan Bershad, 2 Stonebridge Rd., Montclair, N.J. 07042

[21] Appl. No.: 09/123,589

[22] Filed: Jul. 28, 1998

[51] Int. Cl.[7] .......................... A01N 43/40; A01N 43/06; A01N 43/58

[52] U.S. Cl. .......................... 514/356; 514/356; 514/337; 514/444; 514/247; 514/871; 514/859; 536/24.3; 435/6

[58] Field of Search .................. 435/6, 91.2; 536/24, 536/24.3; 514/337, 444, 356, 247, 871, 859

[56] References Cited

U.S. PATENT DOCUMENTS 5,089,509  2/1992  Chandraratna .

OTHER PUBLICATIONS

Leyden, James J., Emerging Topical Retinoid Therapies, Journal of the American Academy of Dermatology, Apr. 1998, vol. 38, No. 4, pp. S1–S4.

Chandraratna, R., Tazarotene—first of a new generation of receptor–selective retinoids, British Journal of Dermatology 1996, vol. 135, pp. 18–25.

Topical Retinoid Therapy, National Psoriasis Foundation, 1997, pp. 1–6.

*Primary Examiner*—Keith D. MacMillan
*Assistant Examiner*—Vickie Kim
*Attorney, Agent, or Firm*—Kenyon & Kenyon

[57] ABSTRACT

The present invention relates to a method of treating acne using short-term contact with an acetylenic retinoid, preferably tazarotene and related compounds.

7 Claims, No Drawings

SHORT CONTACT TREATMENT FOR ACNE

BACKGROUND OF THE INVENTION

The present invention is directed to the treatment of various chronic and acute skin conditions, particularly acne and photoaging.

There is presently in use an FDA approved treatment for acne employing tazarotene topical gel that is marketed by Allergan, Inc. under the brand name Tazorac™.

Tazarotene has the following chemical formula:

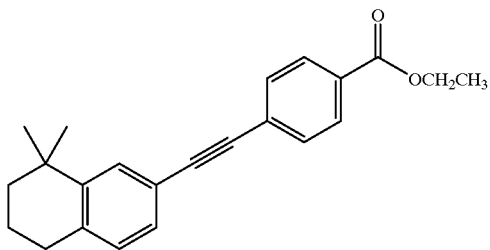

and is described by the chemical name: ethyl 6-[2-(4,4-dimethylthiochroman-6-yl)-ethynyl nicotinate. ($C_{21}H_{21}NO_2S$). Tazorac™ gel is commercially available in 0.05% and 0.1% formulations by weight of tazarotene, with 1.0% benzyl alcohol as a preservative and the following inactive ingredients: ascorbic acid, butylated hydroxyanisole, butylated hydroxytoluene, carbomer 934P, edetate disodium, hexylene glycol, purified water, poloxamer 407, polyethylene glycol 400, polysorbate 40, and tromethamine.

Tazarotene is a retinoid prodrug which is converted to its active form—the cognate carboxylic acid of tazarotene (AGN 190299)—by rapid deesterification in most biological systems. AGN 190299 binds to all three members of the retinoic acid receptor (RAR) family; $RAR_\alpha$, $RAR_\beta$ and $RAR_\gamma$, but shows relative selectivity for $RAR_\beta$ and $RAR_\gamma$, and may modify gene expression. The clinical significance of these findings is not known.

The mechanism of action in the treatment of acne and photoaging with tazarotene is not known. The current FDA-approved therapeutic regimen requires Tazorac™ gel to be applied topically in its 0.05% or its 0.1% formulation and left on the affected skin for long periods of time, e.g. overnight. It is generally applied in the evening and left in place until routine washing in the morning. Thus, in the treatment of acne, the Tazorac™ gel would typically be left on the skin for 8 to 12 hours.

Unfortunately, a major shortcoming of this course of treatment is that adverse skin reactions are experienced by a significant portion of users. These reactions include pruritus, burning/stinging and erythema (sometimes severe). Since the treatment regimen is usually prolonged, covering many weeks or months, any adverse reactions are rendered even more substantial in the perception of the user, often resulting in the interruption or abandonment of the treatment regimen. Thus the adverse reactions are not merely significant in-and-of themselves, but may make treatment ineffectual due to the inability or unwillingness of the user to follow the regimen.

DESCRIPTION OF THE INVENTION

According to the invention, it has been found that short-contact tazarotene therapy yields surprisingly improved and beneficial results in the treatment of acne. It has further been found that the short-contact tazarotene therapy actually reduces and even reverses the effects of sun-induced aging (photoaging).

"Short-contact tazarotene therapy", as used herein, is intended to distinguish over conventional, or extended-contact, treatment(s) with tazarotene, wherein Tazorac™ gel is applied to a patient's skin (typically once a day) and left on the skin indefinitely or until routine washing or showering occurs after a prolonged period of time (typically overnight).

In accordance with the invention, short-contact tazarotene therapy thus comprises the steps of applying a tazarotene composition to an affected area of the skin for a brief time period followed by rinsing of the skin/affected area. In the case of acne, the usual contact time is of from about 30 seconds to about 15 minutes, preferably for a period of from about 2 to about 5 minutes. In the case of photoaging, the usual contact time is from about 30 seconds to about 10 minutes, preferably for about 1 to about 3 minutes. Immediately following the prescribed period of time, the skin is rinsed thoroughly, typically with lukewarm water.

In accordance with the invention and as used herein, a "tazarotene composition" comprises acetylenic retinoid compounds, or pharmaceutically-acceptable salts thereof, in admixture with a pharmaceutically acceptable carrier. The acetylenic retinoids of the invention are the compounds of formula I as represented by

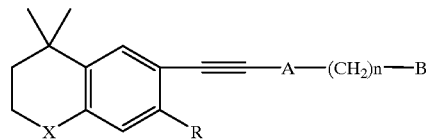

wherein X is S, O, or NR' where R' is hydrogen or lower alkyl; R is hydrogen or lower alkyl; A is pyridinyl, thienyl, furyl, pyridazinyl, pyrimidinyl or pyrazinyl; n is 0–2; and B is H, —COOH or a pharmaceutically acceptable salt, ester or amide thereof, —$H_2OH$ or an ether or ester derivative, or —CHO or an acetal derivative, or —$COR_1$ or a ketal derivative where $R_1$ is —$(CH_2)_mCH_3$ where m is 0–4. Hence the tazarotene compositions of the invention are not limited only to tazarotene but rather may contain any acetylenic retinoid, and preferably contains those represented by Formula I.

The term "ester" as used here refers to and covers any compound falling within the definition of that term as classically used in organic chemistry. Where A is —COOH, this term covers the products derived from treatment of this function with alcohols. Where the ester is derived from compounds where A is —$CH_2OH$, this term covers compounds of the formula—$CH_2OOCR$ where R is any substituted or unsubstituted aliphatic, aromatic or aliphatic-aromatic group.

Preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Here, and where ever else used, lower alkyl means having 1–6 carbon atoms. Also preferred are the phenyl or lower alkylphenyl esters.

The term "amide" has the meaning generally accorded that term in organic chemistry. In this instance it includes the unsubstituted amides and all aliphatic and aromatic mono- and di-substituted amides. Preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from lower alkyl amines. Also preferred are mono- and di-substituted amides derived from the phenyl or lower alkylphenyl amines. Unsubstituted amides are also preferred.

Acetals and ketals includes the radicals of the formula—CK where K is (—OR)$_2$. Here, R is lower alkyl. Also, K may be—OR$_1$O—where R$_1$ is lower alkyl of 2–5 carbon atoms, straight chain or branched.

A pharmaceutically acceptable salt may be prepared for any compound of this invention having a functionality capable of forming such salt, for example an acid or amine functionality. A pharmaceutically acceptable salt may be any salt which retains the activity of the parent compound and does not impart any deleterious or untoward effect on the subject to which it is administered and in the context in which it is administered.

The preferred acetylenic retinoid compounds of this invention are those where the ethynyl group and the B group are attached to the 2 and 5 positions respectively of a pyridine ring (the 6 and 3 positions in the nicotinic acid nomenclature being equivalent to the 2/5 designation in the pyridine nomenclature) or the 5 and 2 positions respectively of a thiophene group respectively; n is 0; and B is—COOH, an alkali metal salt or organic amine salt, or a lower alkyl ester, or —CH$_2$OH and the lower alkyl esters and ethers thereof, or—CHO and acetal derivatives thereof.

The preferred compounds include:
ethyl 6-(2-(4,4-dimethylthiochroman-6-yl)ethynyl)-nicotinate;
6-(2-(4,4-dimethylthiochroman-6-yl)ehtynyl)nicotinic acid;
ethyl 6-(2-(4,4-dimethylchroman-6-yl)ethynyl)nicotinate;
ethyl 6-(2-(4,4,7-trimethylthiochroman-6-yl)ethynyl)-nicotinate;
ethyl 6-(2-(4,4-dimethyl- 1,2,3,4-tetrahydroquinolin-6-yl) ethynyl)nicotinate;
ethyl 5-(2-(4,4-dimethylthiochroman-6-yl)ethynyl) thiophene-2-carboxylate;
6-(2-4,4-dimethylthiochroman-6-yl)-ethynyl)-3-pyridylmethanol; and
2-(2-(4,4-dimethylthiochroman-6-yl)-ethynyl)-5-pyridinecarboxaldehyde.

The most preferred compound is ethyl 6-(2-(4,4-dimethylthiochroman-6-yl)ethynyl)-nicotinate, also known as tazarotene.

The compounds of the invention can be made by methods known in the art. One means to make such compounds is provided in U.S. Pat. No. 5,089,509 which is incorporated herein by reference.

The "tazarotene composition" contains an acetylenic retinoid compound in an amount suitable for topical use on humans. Such compositions may be in the form of a gel, cream, lotion, ointment, cleanser or solution and include a variety of preservatives, carriers and other inactive or active ingredients.

As demonstrated by the following examples, surprisingly good results are obtainable using short-contact tazarotene therapy. Not only does it appear that there is no loss of effectiveness of the active tazarotene ingredient (as compared with conventional extended-contact therapy), but also that the effectiveness may be enhanced in some instances. Even more important, the adverse reactions are substantially reduced to tolerable or even negligible levels, thereby resulting in the ability and willingness of the user to adhere to the novel regimen. This combination of effects, i.e., equal or enhanced effectiveness, reduction in adverse reactions, and regimen adherence, yields surprisingly improved therapeutic efficacy.

EXAMPLE 1

Twenty (20) acne patients were treated with Tazorac™ (0.05% or 0.1%). They applied the gel to the facial skin once or twice daily for two to five minutes. Immediately following treatment, the treated skin was thoroughly washed with lukewarm water (the use of washcloth was not recommended, both because of its abrasiveness and tendency to retain the gel). The results following four weeks of therapy were as follows;

1. Signs of retinization (slight reddening, peeling, and irritation) occurred in 11 of 20 patients during the first 2 weeks of short-contact tazarotene therapy. 10 of these 11 reported only minor discomfort, but one reported marked redness and irritation.
2. Subjective improvement of acne occurred in 18 of 20 patients, usually by 2 to 3 weeks of therapy. One patient with recalcitrant acne of ten years duration had an 80% reduction in lesion counts within 3 weeks. 8 of 20 patients had greater than 75% reduction in lesion counts, 6 of 20 had greater than 50% reduction in lesion counts, and 4 of 20 had greater than 25% reduction in lesion counts after 4 weeks or more of short-contact tazarotene therapy.
3. One patient with adult acne and photoaging noted subjective improvement in skin texture and pigmentation after 4 weeks of therapy.
4. 19 of 20 patients viewed the short-contact tazarotene therapy as pleasant and convenient.

EXAMPLE 2

As noted in Example 1, at least one of the patients noticed the improvement of skin damaged by the effects of photoaging. Similar effects are observed in other patients following the short-contact tazarotene therapy. The contact period is from 30-seconds to ten minutes, preferably one to three minutes, followed immediately by rinsing. Once or, preferably, twice per day treatment is recommended.

In addition to the patient noted in Example 1, two other patients have been treated with short-contact tazarotene therapy for photoaging, for a period of six weeks or longer. All three patients were examined and photographed at several intervals, and were found to have noticeable improvement in skin texture and pigmentation, a reduction in fine wrinkling and apparent diminution of solar keratoses, which are believed to be precancerous lesions.

I claim:

1. A method of treating acne in a human patient comprising the steps of (1) topically applying an effective amount of a tazarotene composition to the affected area of a patient's skin; (2) allowing said composition to remain in contact with the skin for a period of from about thirty seconds to about 15 minutes; and (3) rinsing said tazarotene composition from said affected area.

2. The method according to claim 1 wherein said composition remains in contact with the skin for a period of from about two to about five minutes.

3. The method according to claim 1 wherein said composition comprises about 0.05% tazarotene.

4. The method according to claim 2 wherein said composition comprises about 0.05% tazarotene.

5. The method according to claim 1 wherein said composition comprises about 0.1% tazarotene.

6. The method according to claim 2 wherein said composition comprises about 0.1% tazarotene.

7. The method according to any one of claims 1–6, wherein steps (1) to (3) are carried out at least 3 times per week.

* * * * *